United States Patent [19]

Sieber

[11] Patent Number: 5,776,360
[45] Date of Patent: Jul. 7, 1998

[54] HIGHLY DISPERSE MAGNETIC METAL OXIDE PARTICLES, PROCESSES FOR THEIR PREPARATION AND THEIR USE

[75] Inventor: Werner Sieber, Fribourg, Switzerland

[73] Assignee: Chiron Diagnostics Corporation, East Walpole, Mass.

[21] Appl. No.: 765,091

[22] PCT Filed: Jun. 22, 1995

[86] PCT No.: PCT/EP95/02441

§ 371 Date: Jan. 3, 1997

§ 102(e) Date: Jan. 3, 1997

[87] PCT Pub. No.: WO96/02060

PCT Pub. Date: Jan. 25, 1996

[30] Foreign Application Priority Data

Jul. 7, 1994 [CH] Switzerland .................. 2176/94

[51] Int. Cl.⁶ .................. H01F 1/36; H01F 1/44; B03C 1/01; G01N 33/543
[52] U.S. Cl. .................. 252/62.63; 252/62.56; 252/62.54; 252/313.1; 436/526; 427/215; 427/220; 428/405
[58] Field of Search .................. 428/405; 427/215, 427/220; 252/62.56, 62.54, 62.52, 62.63, 313.1; 436/526

[56] References Cited

U.S. PATENT DOCUMENTS

| | | | |
|---|---|---|---|
| 4,554,088 | 11/1985 | Whitehead et al. | 252/62.54 |
| 4,795,698 | 1/1989 | Owen et al. | 435/4 |
| 5,013,471 | 5/1991 | Ogawa | 252/62.52 |
| 5,206,159 | 4/1993 | Cohen et al. | 435/180 |

FOREIGN PATENT DOCUMENTS

| | | |
|---|---|---|
| 275285 | 1/1988 | European Pat. Off. |
| 0420186 | 9/1990 | European Pat. Off. |
| 0585868 | 8/1993 | European Pat. Off. |
| WO90/15666 | 1/1996 | WIPO |

Primary Examiner—Melissa Bonner
Attorney, Agent, or Firm—Arthur S. Morgenstern; Robert P. Blackburn

[57] ABSTRACT

This invention relates to magnetic particles comprising mixed oxides of divalent metals and iron (III), having a diameter of 1–10 nm and a surface area of 120–350 m²/g, with silanes bound to the surface of said particle. It also relates to (1) the process for making said particles by simultaneous precipitation and silanization from aqueous solution and (2) their use as carrier materials for the magnetic separation of substances immobilized therewith.

38 Claims, No Drawings

HIGHLY DISPERSE MAGNETIC METAL OXIDE PARTICLES, PROCESSES FOR THEIR PREPARATION AND THEIR USE

The present invention relates to magnetic particles comprising mixed oxides of divalent metals and iron(III) oxide having a particle diameter in the region of a few nanometers and a large surface area, to whose surface functional silanes are bound; a process for their preparation by simultaneous precipitation and silanization from aqueous solution; and their use as carrier material for the magnetic separation of substances immobilized therewith.

The term magnetic means that the particles have permanent magnetism, paramagnetism or superparamagnetism and react to magnetic fields.

Oxidic ferrites have long been known as magnetic materials. Such materials are described, for example, in Gmelins Handbuch der anorganischen Chemie, System No. 59, Verlag Chemie GmbH, Weinheim (1959), page 59 et seq. The most well known ferromagnetic materials are metal(II) ferrites, for example magnetite and $\gamma$-$Fe_2O_3$, which forms a continuous mixed series with ferrites. The ferrites may contain one or more metal(II) cations, and these themselves may be partly replaced by monovalent metal cations, for example lithium.

It has been known for a relatively long time that substances, particularly bioactive substances, for example drugs, cells, antibodies, oligo- and polynucleic acids, nucleotides, enzymes, vitamins, cofactors and proteins, can be immobilized on magnetic particles, for example magnetite, and can be separated off under the influence of magnetic fields for the analysis or diagnosis of admixed or undesired substances. Furthermore, highly disperse magnetic particles are also used as contrast media in visualizations by means of nuclear spin resonance methods (cf. WO 91/02811). In the case of in vivo applications, small particles are required in order to be able to pass through even very small pores. However, a small particle diameter is also desirable for achieving a high loading during immobilization.

U.S. Pat. No. 4,554,088 describes for this purpose magnetite particles which are functionally silanized at the surface and have particle diameters of about 50 nm and high diameters and a specific surface area of about 120 to 140 $m^2/g$. The particle diameter and the relatively small surface area are regarded as being too small for many applications, particularly in vivo applications.

In Journal of Colloid and Interface Science, Vol. 141, No. 2, pages 505 to 511, H. Kobayashi et al. describe microfine magnetite particles which are modified with aminosilanes and have diameters in the range of 10–15 nm but which only have specific surface areas of 77 to 99 $m^2/g$ and are used for the immobilization of enzymes.

The modified magnetites are prepared by a two-stage process in which the magnetites are first formed by precipitation from aqueous metal salt solutions, and their surfaces are then modified in a second stage with functional silanes.

It has now surprisingly been found that magnetite particles which have diameters of 10 mm or less in combination with substantially larger specific surface areas and which can be loaded to a higher degree and are more suitable for separations and applications, particularly in vivo ones, are obtained if the silanization is carried out simultaneously with the precipitation of the mixed oxides. The mean size of the particles is surprisingly considerably smaller than in a process with the addition of silane. Furthermore, the crystallization of the magnetic particles is not adversely affected by the presence of the silane. Surprisingly, however, the silane is simultaneously bound to the mixed oxides in such a way that the functional groups at the surface are accessible to further reactions. It has also been found that these silanized magnetic particles have an extremely high dispersion stability and do not form any sediment over long periods.

The invention provides magnetic particles of mixed oxides from the group comprising the ferrites, which have a particle diameter of 1 to 10 nm and a specific surface area of 120 to 350 $m^2/g$ and to whose surface functional silanes are bound.

The functional silanes may be adsorptively and/or covalently bound to the surface of the mixed oxide. Covalent bonding is effected essentially via siloxane bonds. For the purposes of the invention, the term functional means that at least one group —$R_3$—$Y_1$ is covalently bonded to the Si atom, and $Y_1$ is a functional group, for example —CH=$CH_2$, —OH, —$NH_2$, —NCO, —NCS or

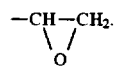

Functional groups stable to hydrolysis are preferred.

The particle diameter is preferably 2 to 8 nm and particularly preferably 2 to 6 nm. The specific surface area is preferably 150 to 330 $m^2/g$ and particularly preferably 200 to 330 $m^2/g$. The specific surface area is determined by adsorption of nitrogen by the BET method. This method is known to those skilled in the art and is described here The amount of silane may be, for example 0.1 to 30% by weight, preferably 0.5 to 25 and particularly preferably 1 to 20% by weight, based on the mixed oxide.

The ferrites may be, for example, those of the formula I or mixtures of ferrites of the formula I $$MeOFe_2O_3 \qquad (I)$$

in which Me is a divalent metal atom forming a ferrite, preferably Zn, Cd, V, Fe, Ni, Cu, Co, Sr, Ca or Mg, particularly preferably Mn, Zn, Ni or Co. Me is particularly preferably Fe; the ferrites are then the very particularly preferred magnetites. In another embodiment, they are $\gamma$-$Fe_2O_3$ itself or mixed crystals of $\gamma$-$Fe_2O_3$ with magnetite.

The silanes bound to the surface may be derived, for example, from compounds of the formula II $$SiR_1R_2R_4—R_3—Y \qquad (II)$$

in which $R_1$, $R_2$ and $R_4$, independently of one another, are $C_1$–$C_{12}$alkoxy or halogen, $R_3$ is $C_2$–$C_{12}$alkylene or phenylene and Y is —OH, —$NH_2$, —NH($C_1$–$C_4$alkyl), —NH—$C_2$–$C_4$alkylene—$NH_2$, —NH—$C_2$–$C_4$alkylene—NH($C_1$–$C_4$alkyl) or —NH—$C_2$–$C_4$alkylene—OH.

If covalent bonds are formed, at least one of $R_1$, $R_2$ and $R_4$ is a bridge oxygen atom.

Alkoxy $R_1$, $R_2$ and $R_4$ are preferably $C_1$–$C_8$alkoxy and particularly preferably $C_1$–$C_4$alkoxy. Examples of alkoxy, which is preferably linear, are methoxy, ethoxy, propoxy, butoxy, pentyloxy, hexyloxy, octyloxy, decyloxy and dodecyloxy.

Halogen is preferably Cl or Br and particularly preferably Cl.

In a preferred embodiment, $R_1$, $R_2$ and $R_4$, independently of one another, are $C_1$–$C_4$alkoxy, in particular methoxy or ethoxy, or Cl.

Particularly preferably, $R_1$ and $R_2$ independently of one another are $C_1$–$C_4$alkoxy, in particularly methoxy or ethoxy.

Alkylene $R_3$, which is preferably linear, is in particular $C_2$–$C_8$alkylene and particularly preferably $C_2$–$C_4$alkylene. Some examples are ethylene, 1,2- and 1,3-propylene, 1,2-, 1,3- or 1,4-butylene, pentylene, hexylene, octylene, decylene and dodecylene. Ethylene, 1,3-propylene and 1,4-butylene are particularly preferred and 1,3-propylene is very particularly prefers In a preferred embodiment, $R_3$ is $C_2$–$C_4$alkylene, in particular 1,3-propylene or 1,4-butylene, 1,3- or 1,4-phenylene.

Alkyl in the groups —NH($C_1$–$C_4$alkyl) and —NH—$C_2$–$C_4$alkylene—NH($C_1$–$C_4$alkyl) is preferably methyl. Alkylene in the groups —NH—$C_2$–$C_4$alkylene—NH$_2$, —NH—$C_2$–$C_4$alkylene—NH($C_1$–$C_4$alkyl) and —NH—$C_2$–$C_4$alkylene—OH is preferably ethylene or 1,2-propylene.

Y is preferably —NH$_2$ or —NH—$C_2$–$C_4$alkylene—NH$_2$.

A preferred subgroup of the radicals of the formula II are those in which $R_1$ and $R_2$, independently of one another, are methoxy or ethoxy. $R_3$ is 1,3-propylene, 1,4-butylene or 1,4-phenylene and Y is —NH$_2$ or —NH—ethylene—NH$_2$. Very particularly preferably, $R_1$ and $R_2$ independently of one another are methoxy or ethoxy, $R_3$ is 1,3-propylene or 1,4-butylene, and Y is —NH$_2$ or —NH—ethylene—NH$_2$.

The magnetic mixed oxides according to the invention have essentially a spherical external shape.

The magnetic mixed oxide particles according to the invention are surprisingly obtained by a simple process in which the precipitation of the mixed oxides from their aqueous solutions with hydroxides is carried out in the presence of a hydrolysable silane having a functional group stable to hydrolysis.

The invention also provides a process for the preparation of the magnetic mixed oxides according to the invention, which comprises (1) dissolving a water-soluble metal salt of a divalent metal forming a ferrite and a water-soluble Fe(III) salt in water, (2) preparing an aqueous alkaline solution, (3) mixing the solution (1) or (2) or both solutions with a functional silane of the formula III

$$(X)_{3-n}Si—R_3—Y \qquad (III)$$

in which n is 0, 1 or 2, X, as a leaving group, is $C_1$–$C_{12}$alkoxy or halogen and $R_3$ and Y are as defined above, and (4) introducing the solutions (1) and (2), at least one of which comprises a functional silane, into a reaction vessel, allowing the reaction mixture to react and isolating the mixed oxide after the end of the reaction.

In the compounds of the formula III, n is preferably 0.

The metal salts and iron(III) salts are preferably inorganic salts, particularly preferably salts of mineral acids and inorganic oxo acids, for example chlorides, bromides, nitrites, nitrates, sulfites, sulfates, bisulfates, pyrosulfates, thiosulfates, perchlorates, perbromates, periodates, phosphites, hydrogen phosphates, hydrogen phosphites, cyanides and thiocyanates. The metal salts and the Fe(III) salt must be hydrolysable in an alkaline medium. Preferred metal salts are the sulfates and the preferred Fe(III) salt is the chloride.

The leaving group X may, be for example, chloride or bromide, or may be $C_1$–$C_4$alkoxy, particularly preferably methoxy.

The reactants are known and in some cases are commercially available or can be prepared by known processes. The functional group in the silane can also be modified after the reaction; for example, amino groups can be converted into cyanate or isothiocyanate groups in a known manner.

In addition to water, the reaction mixture may contain other water-miscible solvents, for example alcohols (methanol, ethanol, ethylene glycol) or ethers (diethyl ether, tetrahydrofuran).

In an advantageous embodiment, the functional silane is added only to the aqueous alkaline solution. The bases used may be alkali metal and alkaline earth metal bases, ammonium hydroxide and the hydroxides of primary, secondary and tertiary $C_1$–$C_4$alkylamines, preferably $C_1$- or $C_2$alkylamines, quaternary $C_1$–$C_4$ammonium bases, preferably $C_1$- or $C_2$ammonium bases. Alkali metal hydroxides and ammonium hydroxide are preferred, and NaOH and KOH are particularly preferred. The bases are added in an amount which is sufficient for hydrolysis of the three reaction components (metal salt, Fe(III) salt and silane) (i.e. in at least equimolar amounts), i.e. 2 mol per mole of metal salt, 3 mol per mole of Fe(III) salt and 1 to 3 mol per mole of silane, depending on the number of leaving groups. It may be advantageous to use an excess, for example up to a 10 mol excess, preferably up to a 5 mol excess, of base, based on the reactants.

The molar ratio of the divalent metal salts to the Fe(III) salt is preferably 1:1 to 1:4, particularly preferably 1:1.5 to 1:4.

The reaction temperature may be, for example, from room temperature to 100° C., preferably from 30° to 80° C. and particularly preferably 40° to 70° C. The solutions can expediently be preheated before mixing, for example up to the reaction temperature.

The process can be carried out by combining the solutions directly in the reaction vessel, which may be effected all at once by pouring in or more slowly by simultaneous dropwise addition. In an advantageous embodiment of the process according to the invention, the solutions are premixed before they reach the reaction vessel, which is advantageously associated with continuous addition. Mixing can be carried out, for example, by joining the feed lines from the storage containers before the reaction vessel, for example by means of a Y-shaped connector or an overflow vessel with, if desired, a stirring means. Water is advantageously initially taken in the reaction vessel to ensure rapid thorough mixing of the solutions. For thorough mixing, the reaction mixture is expediently stirred After mixing, the reaction mixture is allowed to react while stirring, the reaction temperature advantageously being maintained. The product can then be isolated and purified in a known manner. For isolation, the solid product can, for example, be centrifuged or exposed to an inhomogeneous magnetic field so that the solid highly disperse particles settle out on the bottom. The supernatant on solution can then be decant For purification, the product can be suspended once or several times in water and isolated again in the same manner. For the preparation of a highly pure product, the product isolated in this manner is expediently dialysed with demineralized water, it being possible to determine the purity by determining the conductivity of the water.

In the case of the product according to the invention sufficient dilution results in the formation of colloidal clear suspensions which have virtually unlimited stability. By adding electrolytes, for example salts (NaCl), the particles can be flocculated from these suspensions again. The particle sizes and the magnetic responsivity are not substantially influenced either by isolation or by storage. They have very high loading capacities. Owing to their small size, they are capable of passing through very small pores and even membranes, for example cell walls. Because of the small size the particles are even no longer recognized as foreign bodies by defensive cells of warm-blooded animals and ar not attacked. The mixed oxide particles according to the invention, in particular the magnetites, are not permanently magnetized under the influence of a magnetic field (superparamagnetism) and can therefore readily be redispersed without formation of agglomerates to give colloidal suspensions, which makes it possible to reuse them. The larger surface area per unit mass permits the binding of larger amounts of organic functional compounds, resulting in higher sensitivity in analytical determinations and greater effectiveness when used as a carrier. The relatively small particle size results in slower sedimentation and easier penetration into biological tissues. The simple preparation process and combination of the process steps involving silanization and precipitation of the mixed oxide very considerably reduce the amounts of reaction residues and wash solutions to be disposed of.

The magnetic mixed oxide particles according to the invention are outstandingly suitable as solid carrier materials for binding to organic and in particular biological substances having specific affinities or the capability of adsorption or of interaction with other organic or biological molecules which are to be separated and detected or transported to certain places by means of magnetic fields. They may be used both in in vitro and in in vivo systems. The mixed oxide particles can be used, for example, in immunological assays or other biological assays, in biochemical or enzymatic reactions, for purification in affinity chromatography or for cell separation or cell sorting or used for diagnostic and therapeutic purposes. Such applications and the immobilization (coupling) of substances to the mixed oxide particles are described, for example, in U.S. Pat. No. 4,554,088. Processes for binding or coupling molecules to the functional silane groups are described, for example, by H. H. Weethall et al. in Applied Biochemistry and Biotechnology, Volume 22, pages 311 to 331.

The mixed oxide particles according to the invention can be used for diagnostic purposes in the form of a suspension also after appropriate modification [cf. L. X. Tiefenauer et al., Bioconjugate Chem., 4, pages 347 to 352 (1993)] of the surface with suitable indicator substances as contrast media in nuclear spin resonance, electron spin resonance and electron microscopy.

The invention also provides the use of magnetic mixed oxide particles as carrier material for the immobilization of organic and biological substances.

The invention also provides an aqueous dispersion of magnetic particles of mixed oxides from the group comprising the ferrites which have a particle diameter of 1 to 10 nm and a specific surface area of 120 to 350 $m^2/g$ and to whose surface functional silanes are bound.

The aqueous dispersion comprises the mixed oxides preferably in an amount of 0.1 to 60% by weight, particularly 0.5 to 40% by weight, based on the total mixture.

In addition to the possible uses mentioned, the dispersions according to the invention can be used as magnetic fluids (cf. R. E. Rosensweig in Chemical Engineering Progress (1989), pages 53 to 61).

The following examples illustrate the invention in more detail. The particle sizes are determined by means of high-resolution electron microscopy and by X-ray diffraction, from the line width.

A) PREPARATION EXAMPLES

Example A1

Simultaneous precipitation and silanization of magnetite.

A 1.5 l round-bottomed flask (reaction flask) and two 0.5 l round-bottomed flasks (storage flasks), each equipped with a magnetic stirrer, are placed in a thermostated oil bath. The 0.5 l flasks are provided with glass tubes which extend virtually to the bottom. The glass tubes are provided with plastic tubes which are passed through a double pump. The ends of the plastic tubes are connected to the two ends of a glass Y-piece whose outlet is connected to a glass tube which is led into a 1.5 l round-bottomed flask.

In the first 0.5 l storage flask, 118.2 g of iron(III) chloride hexahydrate and 60.5 g of iron(II) sulfate heptahydrate in are dissolved in 300 ml of water, filtered through a 0.45 μm membrane filter and made up with water to a total amount of 540 g.

In the second storage container, 175 g of NaOH are dissolved in water to give a total amount of 540 g. The solution is cooled to 30° C., and 40 g of $(CH_3O)_3SiCH_2CH_2CH_2NHCH_2CH_2NH_2$ are added while stirring. The clear solution is adjusted to a total amount of 625 g with water.

200 ml of water are introduced into the reaction flask, and all 3 flasks are heated to 50° C. The pump is started and the solutions are pumped into the reaction flask at a flow rate of about 200 ml/minute for about 5 minutes (equal to mixing time). The reaction mixture is stirred for a further 2 hours at 50° C., then cooled and then transferred to a beaker and diluted to 2.8 l with water. The solid product is caused to settle out on the bottom of the vessel by means of a magnet, and the supernatant solution is decanted. The solid is suspended twice in water and decanted. It is then taken up again in water and the suspension is dialysed with demineralized water until the conductivity of the wash solution for a centrifuged sample is less than 100 microsiemens/cm.

Colloidal suspensions which have virtually unlimited stability can be prepared from the enriched silanized magnetite particles on dilution with water. NaCl is added to the suspension, the magnetite particles flocculating and being separated off by the use of an inhomogeneous magnetic field.

For analysis, a sample of the product isolated is dried under reduced pressure (about 100 mmHg), first for 24 hours at 60° C. and then for 24 hours at 140° C. The product is comminuted in a mortar and thereafter the carbon content is determined as 2.4%, the nitrogen content as 0.75% and the silicon content as 1.1% by means of elemental analysis. The specific surface area, determined by nitrogen adsorption, is 283 $m^2/g$. Investigations by electron microscopy show that the particle diameter of the virtually spherical particles is about 3 nm.

The dried product is characterized with the aid of X-ay diffraction. The diffraction pattern obtained is in agreement with that of magnetite. The broadening of the lines is in agreement with a particle size of about 3 nm.

Example A2

Example A1 is repeated, but 106.4 g of $FeCl_3$—6 $H_2O$ and 60 g of $(CH_3O)_3SiC_2CH_2CH_2NHCH_2CH_2NH_2$ are used. The product obtained has a specific surface of 288 $m^2/g$. Particle size: 3–5 nm.

Example A3

Example A2 is repeated, but 45 g of the silane $(C_2H_5O)_3SiCH_2CH_2CH_2NH_2$ are used. The product obtained has a specific surface area of 304 $m^2/g$. Particle size: 5 nm.

Example A4

Example A1 is repeated, but 60 g of $FeCl_3$.6 $H_2O$ and 325 g of $FeSO_4$.7 $H_2O$ and in addition 10 g of LiCl are used. The NaOH solution used, comprising 90 g of NaOH in 360 g of solution, is additionally saturated with $Ba(OH)_2$. The amount of silane is 20 mL. The product obtained has a specific surface area of 283 $m^2/g$. Elemental analysis: 2.7% by weight of C, 0.93% by weight of N, 1.26% by weight of Si, 4.2% by weight of Ba and 460 ppm of Li. Particle size: 6 nm.

Example A5

Example A1 is repeated, but 60 g of $FeCl_3 \cdot 6\, H_2O$ and 32.5 g of $FeSO_4 \cdot 7\, H_2O$ are used. The base used is a solution of 190 g of KOH in 300 ml of water. 10 g of $NaSO_3$ are furthermore added to this solution in order to prevent oxidation of the silane. The silane used is p-aminophenyltrimethoxysilane (20 ml). After dissolution of the silane, the solution is made up to 550 ml with water and then combined with the iron solution. The product obtained has a specific surface area of 289 $m^2/g$ and a mean particle size of 3 to 5 nm. Elemental analysis: 2.84% by weight of C, 0.46% by weight of N and 1.33% by weight of Si.

Example A6

Example A1 is repeated, but 14.65 g of $FeCl_3 \cdot 6\, H_2O$ and 5.69 g of $FeCl_2 \cdot 4\, H_2O$ in a solution volume of 200 ml are used. 200 ml of a 25% tetraethylammonium hydroxide solution serve as the base. The amount of silane is 4 ml. The resulting dried magnetic product comprises 87.2% of $Fe_3O_4$, 2.32% of C, 0.71% of N and 1.13% of Si. The specific surface area is 304 $m^2/g$. The X-ray diffraction pattern shows a pure, well crystallized ferrite phase having a particle diameter of about 3 nm. The particle size is confirmed by electron micrographs.

Example A7

Example A1 is repeated, but 60 g of $FeCl_3 \cdot 6\, H_2O$ and 27.5 g of $CoCl_2 \cdot 6\, H_2O$ are used. In addition, the air in the reaction vessel is displaced by nitrogen. The base used is a solution of 90 g of NaOH in 300 ml of water, and the amount of silane is 20 ml. The result is a suspension of particles which are attracted by a magnet. The specific surface area of the dried product is 301 $m^2/g$.

Example A8

Example A1 is repeated, but 60 g of $FeCl_3 \cdot 6\, H_2O$, 13.9 g of $NiCl_2 \cdot 6\, H_2O$ and 16.8 g of $ZnSO_4 \cdot 7\, H_2O$ are used. The base used is a solution of 90 g of NaOH in 300 ml of water, and 20 ml of 3-aminopropyltriethoxysilane are used as the silane. The resulting particles in the dried state have a specific surface area of 242 $m^2/g$. The product comprises 41.6% of Fe, 11.4% of Ni, 10.1% of Z, 2.04% of C, 1.48% of Si and 0.71% of N. The dried product is characterized with the aid of X-ray diffraction. The diffraction pattern agrees with that of pure zinc nickel ferrite. The broadening of the lines is in agreement with the particle size of about 3 nm.

Example A9

Example A1 is repeated, but 32.9 g of $FeCl_3 \cdot 6\, H_2O$ and 17.85 g of $FeSO_4 \cdot 6\, H_2O$ are used, and 20 ml of 4-aminobutyltriethoxysilane are used as the silane. 60 g of NaOH are used as the base. The resulting particles in the dried state have a specific surface area of 300 $m^2/g$. The product purified by dialysis comprises 2.6% of C, 0.55% of N and 1.7% of Si.

B) USE EXAMPLES

Example B1

An amount comprising 10 mg of solid is taken from a suspension according to Example A2. The particles are activated with glutaraldehyde, and 1.6 mg of an HCG (human chorionic gonadotropin) antibody are added (cf. U.S. Pat. No. 4,554,088). 93.4% by weight of the protein are bound. The immobilized antibody is tested for HCG in an automated chemiluminescence apparatus. Solutions having a known HCG content are used as the analyte. The results are shown in Table 1 as "relative light units" (RLU) (measure of the intensity of the chemiluminesence).

Example B2

A suspension according to Example A3 is used and the procedure is as in Example B1.

Example B3

The procedure is as in Example B1, except that only 3.96 mg of solid are used. The protein take-up is 76.7% by weight.

Example B4

The procedure is as in Example B2, except that only 3.76 mg of solid are used. The protein take-up is 58% by weight.

TABLE 1

| | Immunoassay results | | | |
|---|---|---|---|---|
| HCG in analyte (mIU/ml) | B1 RLU | B2 RLU | B3 RLU | B4 RLU |
| 0 | 7359 | 5017 | n.d. | n.d. |
| 50 | 20374 | 13767 | 22977 | 17869 |
| 280 | 66485 | 49949 | 86281 | 80247 |
| 789 | 127741 | 97653 | 196947 | 201495 |
| 1184 | 155810 | 115565 | 289437 | 321146 |

Example B5

Stability of the dispersion

Example A1 is repeated, but 60 g of $FeCl_3 \cdot 6\, H_2O$ and 23.3 g of $FeCl_2 \cdot 4\, H_2O$ are used. The base used is a solution of 90 g of NaOH in 300 ml of water, and the amount of silane is 20 ml. The resulting suspension is dialysed against demineralized water until the conductivity of the supernatant solution is 22 microsiemens/cm. A sample of the suspension which has a solids content of 7.6% is dried. The BET specific surface area is 295 $m^2/g$. The dried product is characterized with the aid of X-ray diffraction. The diffraction pattern obtained agrees with that of magnetite. The broadening of the lines is in agreement with the particle size of about 3 nm.

15 g of the suspension are made up to 180 g with demineralized water, with the addition of 27 ml of 0.1 molar acetic acid, and dispersed by means of an ultrasonic disintegrator (Sonicator W375). The resulting mixture is centrifuged for 30 minutes at 9000 revolutions/minutes. The resulting non-sedimented dispersion has an optical density of 0.48, measured in a 1 mm cell at 600 nm. After 6 weeks, the dispersion is unchanged (no sedimentation).

Example B6

Stability of the dispersion 4.8 g of the dialysed suspension of Example B5 are made up to 60 g with the addition of 0.6 ml of acetic acid and dispersed by means of an ultrasonic disintegrator (Sonicator W375). The resulting mixture is centrifuged for 20 minutes at 5000 revolutions/minute and then for one hour at 9000 revolutions/minute. The resulting non-sedimented dispersion has an optical density of 0.30, measured in a 1 mm cell at 600 mn.

Example B7

Flocculation of a dispersion 4.8 g of the suspension of Example B5 are made up to 60 g with the addition of 0.6 ml of 0.1M acetic acid and 10 g of 0.5 per cent aqueous NaCl solution and dispersed by means of an ultrasonic disintegrator. The mixture is centrifuged for 20 minutes at 5000 revolutions/minute and then for one hour at 9000 revolutions/minute. The resulting clear supernatant solution has an optical density of 0.0, measured in a 1 mm cell at 600 nm.

What is claimed is:

1. A magnetic particle of an iron-based oxide, which has a particle diameter of 1 to less than 5 nm and a specific surface area of about 220 to 350 m²/g and to whose surface functional silanes are bound.

2. A particle according to claim 1, wherein the particle diameter is 3 to less than 5 nm.

3. A particle according to claim 1, wherein the surface area is about 230 to 325 m²/g.

4. A particle according to claim 1, wherein the amount of silane is 0.1 to 30% by weight, based on the mixed oxide.

5. A particle according to claim 1, wherein the order is a ferrite of the formula I $$MeOFe_2O_3 \quad (I)$$

in which Me is a divalent metal atom forming a ferrite or is a mixture of such metal atoms.

6. A particle according to claim 5, wherein, in the formula I, Me is Zn, Cd, V, Fe, Ni, Cu, Co, Ca, Sr, Ba or Mg.

7. A particle according to claim 5, wherein, in formula I, Me is Fe.

8. A particle according to claim 1, wherein the oxide is $\gamma\text{-}Fe_2O_3$ itself or comprises mixed crystals of $\gamma\text{-}Fe_2O_3$ with magnetite.

9. A particle according to claim 1, wherein the silane is derived from a compound of the formula II $$SiR_1R_2R_4\text{---}R_3\text{---}Y \quad (II)$$

in which $R_1$, $R_2$ and $R_4$, independently of one another, are $C_1\text{-}C_{12}$alkoxy or halogen, $R_3$ is $C_2\text{-}C_{12}$alkylene, benzylene or phenylene and Y is —OH, —NH$_2$, —NH(C$_1$-C$_4$alkyl), —NH—C$_2$-C$_4$alkylene—NH$_2$, —NH—C$_2$-C$_4$alkylene—NH(C$_1$-C$_4$alkyl) or —NH—C$_2$-C$_4$alkylene OH.

10. A particle according to claim 9, wherein halogen $R_1$, $R_2$ and $R_4$ are chlorine.

11. A particle according to claim 9, wherein $R_1$, $R_2$ and $R_4$, independently of one another, are $C_1$-$C_4$alkoxy.

12. A particle according to claim 9, wherein $R_1$, $R_2$ and $R_4$, independently of one another, are methoxy or ethoxy.

13. A particle according to claim 9, wherein $R_3$ is $C_2$-$C_4$alkylene or 1,3- or 1,4-phenylene.

14. A particle according to claim 9, wherein $R_3$ is 1,3-propylene or 1,4-butylene.

15. A particle according to claim 9, wherein Y is —NH$_2$ or —NH—C$_2$-C$_4$alkylene-NH$_2$.

16. A particle according to claim 9, wherein $R_1$, $R_2$ and $R_4$, independently of one another, are methoxy or ethoxy, $R_3$ is 1,3-propylene, 1,4-butylene or 1,4-phenylene and Y is —NH$_2$ or —NH—ethylene—NH$_2$.

17. A particle according to claim 16, wherein $R_1$, $R_2$ and $R_4$, independently of one another, are methoxy or ethoxy, $R_3$ is 1,3-propylene or 1,4-butylene and Y is —NH$_2$ or —NH—ethylene—NH$_2$.

18. A process for the preparation of a magnetic mixed oxide according to claim 1, which comprises (1) dissolving a water-soluble metal salt of a ferrite-forming divalent metal and a water-soluble Fe(III) salt in water, (2) preparing an aqueous alkaline solution, (3) mixing the solution (1) or (2) or both solutions with a functional silane corresponding to the following formula III $$(X)_{3-n}Si\text{---}R_3\text{---}y \quad (III)$$

in which n is 0, 1 or 2; X is a leaving group selected from $C_1$-$C_{12}$ alkoxy or halogen and $R_3$ and Y are as defined above, and (4) introducing the solutions (1) and (2), at least one of which comprises a functional silane, into a reaction vessel, allowing the reaction mixture to react and isolating the resulting mixed oxide.

19. A process according to claim 18, wherein the metal salts and iron(III) salts are inorganic salts.

20. A process according to claim 18, wherein the metal salts and iron(III) salts are salts of mineral acids and inorganic oxo acids.

21. A process according to claim 20, wherein the salts used are chlorides, bromides, nitrites, nitrates, sulfites, sulfates, bisulfates, pyrosulfates, thiosulfates, perchlorates, perbromates, periodates, phosphites, hydrogen phosphates, hydrogen phosphites, cyanides and thiocyanates.

22. A process according to claim 18, wherein the metal salts and the Fe(III) salt are hydrolysable in an alkaline medium.

23. A process according to claim 20, wherein the metal salts are sulfates and the Fe(III) salt is a chloride.

24. A process according to claim 18, wherein the leaving group X is halide or $C_1$-$C_4$alkoxy.

25. A process according to claim 24, wherein the leaving group X is chloride, bromide, methoxy or ethoxy.

26. A process according to claim 18, wherein the functional silane is added to the solution (2).

27. A process according to claim 18, wherein said alkaline solution contains an alkali metal or alkaline earth metal base, ammonium hydroxide or the hydroxide of a primary, secondary or tertiary $C_1$-$C_4$alkylamine or a quaternary $C_1$-$C_4$alkylammonium base.

28. A process according to claim 18, wherein said alkaline solution contains an alkali metal hydroxide or ammonium hydroxide.

29. A process according to claim 28, wherein said alkaline solution contains NaOH or KOH.

30. A process according to claim 18, wherein said alkaline solution is added in at least an equimolar amount which is sufficient for hydrolysing the three reaction components, said components being metal salt, Fe(III) salt and silane.

31. A process according to claim 30, wherein said alkaline solution contains an excess, based on the three reaction components.

32. A process according to claim 18, wherein the molar ratio of the divalent metal salts to the Fe(III) salts is 1:1 to 1:4.

33. A process according to claim 18, wherein the reaction temperature is from room temperature to 100° C.

34. A process according to claim 18, wherein the reaction solutions are preheated before being mixed.

35. A method for using the magnetic particles of claim 1 as carrier material for immobilizing organic and biological substances, said method comprising:
   a. activating said particles with glutaraldehyde and
   b. adding said organic or biological substance.

36. An aqueous dispersion of magnetic particles of a mixed oxide from the group comprising ferrites, which has a particle diameter of 1 to less than 5 nm and a specific surface area of about 220 to 350 m$^2$/g and to whose surface functional silanes are bound.

37. An aqueous dispersion according to claim 36, which is present in an amount of 0.1 to 60% by weight, based on the total mixture.

38. An aqueous dispersion according to claim 36, which is present in an amount of 0.5 to 40% by weight.

* * * * *